US00PP28670P2

(12) United States Plant Patent
Humphreys et al.

(10) Patent No.: US PP28,670 P2
(45) Date of Patent: Nov. 21, 2017

(54) ***HEBE* PLANT NAMED 'CELEBRATION'**

(50) Latin Name: ***Hebe* hybrid**
Varietal Denomination: Celebration

(71) Applicants: Stephen Humphreys, Spalding (GB); Yvonne Patricia Humphreys, Spalding (GB)

(72) Inventors: Stephen Humphreys, Spalding (GB); Yvonne Patricia Humphreys, Spalding (GB)

( * ) Notice: Subject to any disclaimer, the term of this patent is extended or adjusted under 35 U.S.C. 154(b) by 0 days.

(21) Appl. No.: 14/999,977

(22) Filed: Jul. 21, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Hebe* named 'Celebration', that is characterized by its compact, well-branched, rounded plant habit, its variegated foliage that is yellow-green in color with green at the center and very thin margins that are red-purple in color, its leaves that are narrowly elliptical to obelliptical in shape, its flowers that transition from dark to light red-purple in color, and its bloom season that commences in mid-May.

2 Drawing Sheets

Botanical classification: *Hebe* hybrid.
Cultivar designation: 'Celebration'.

CROSS REFERENCE TO A RELATED APPLICATION

This application is related to a European plant breeders' rights application filed on Sep. 16, 2014, application No. 2014/2236. There have been no offers for sale anywhere in the world prior to the filing of this Application and no accessibility to one of ordinary skill in the art could have been derived from the printed plant breeder's rights documents.

BACKGROUND OF THE INVENTION

The present invention relates to a new and distinct cultivar of *Hebe* of hybrid origin and known as *Hebe* 'Celebration' and will be referred to hereafter by its cultivar name, 'Celebration'. 'Celebration' is grown for use as a container plant and landscape shrub.

The new cultivar was discovered by one of the Inventors in August of 2009 as a naturally occurring branch mutation of *Hebe* 'Wiri Charm' (not patented) in a production container block at the Inventors' nursery in Spalding, United Kingdom.

Asexual propagation of the new cultivar was first accomplished by one of the Inventors by softwood stem cuttings in Spalding, United Kingdom in March of 2010. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Celebration' as a new and distinct cultivar of *Hebe*.

1. 'Celebration' exhibits a compact, well-branched, rounded plant habit.
2. 'Celebration' exhibits variegated foliage that is yellow-green in color with green at the center and very thin margins that are red-purple in color.
3. 'Celebration' exhibits leaves that are narrowly elliptical to obelliptical in shape.
4. 'Celebration' exhibits flowers that transition from dark to light red-purple in color as they mature.
5. 'Celebration' exhibits a bloom season that commences in mid-May.

The parent plant of 'Celebration', 'Wiri Charm', differs from 'Celebration' in having foliage that is solid green in color, in having leaves that are spear-shaped, in having inflorescences that are larger in size, in having flowers that are pink-purple in color, and in having a later starting bloom period. 'Celebration' can be compared to the *Hebe* cultivars 'Inspiration' and 'Rose Elegance' (both un-patented). 'Inspiration' differs from 'Celebration' in having glossy foliage that is solid green in color, in having flowers that are lavender in color, and in having a later starting bloom period. 'Rose Elegance' differs from 'Celebration' in having glossy foliage that is solid green in color, in having flowers that are pink in color, and, in having inflorescences that are larger in size, and in having a later starting bloom period.

BRIEF DESCRIPTION OF THE DRAWINGS

The accompanying colored photographs illustrate the overall appearance and distinct characteristics of the new *Hebe*. The photographs were taken of a plant approximately six months in age as grown in a 12-liter container in a glass greenhouse Hampshire, The United Kingdom.

The photograph in FIG. 1 is a side view of a plant of 'Celebration'.

Figure 1:
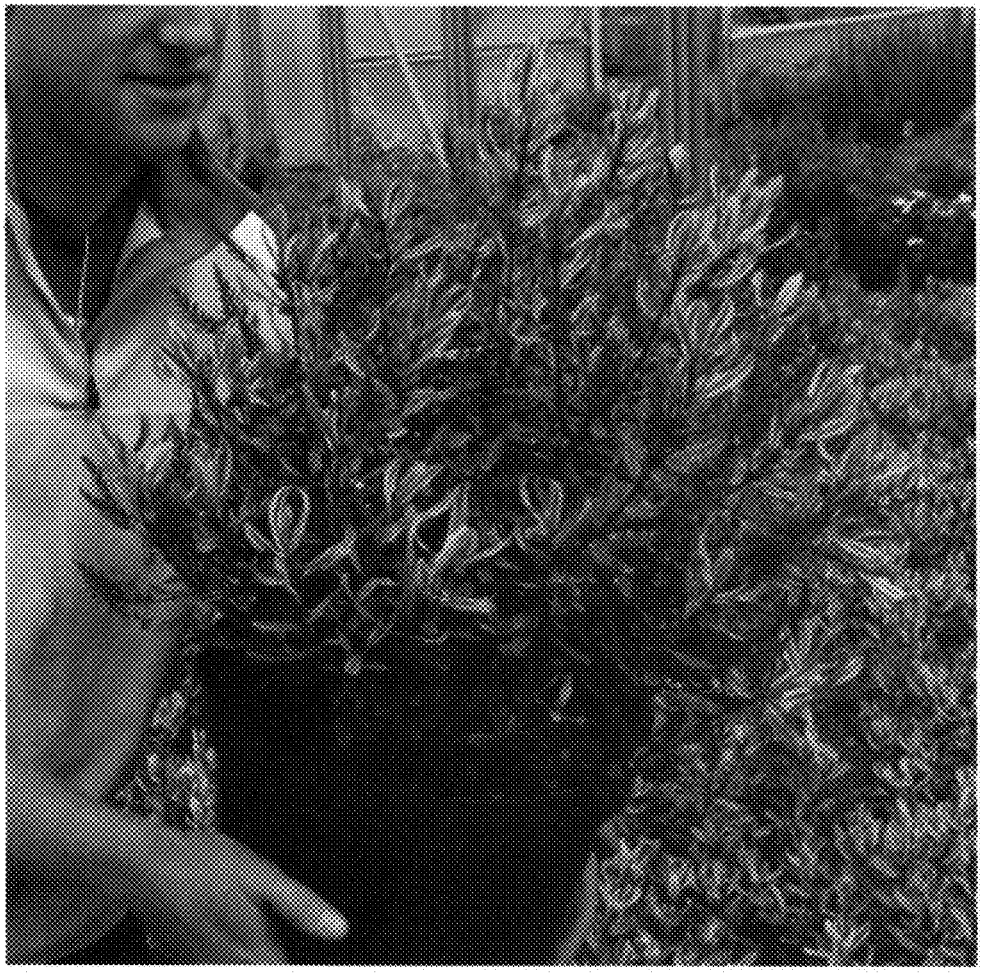
Figure 2:
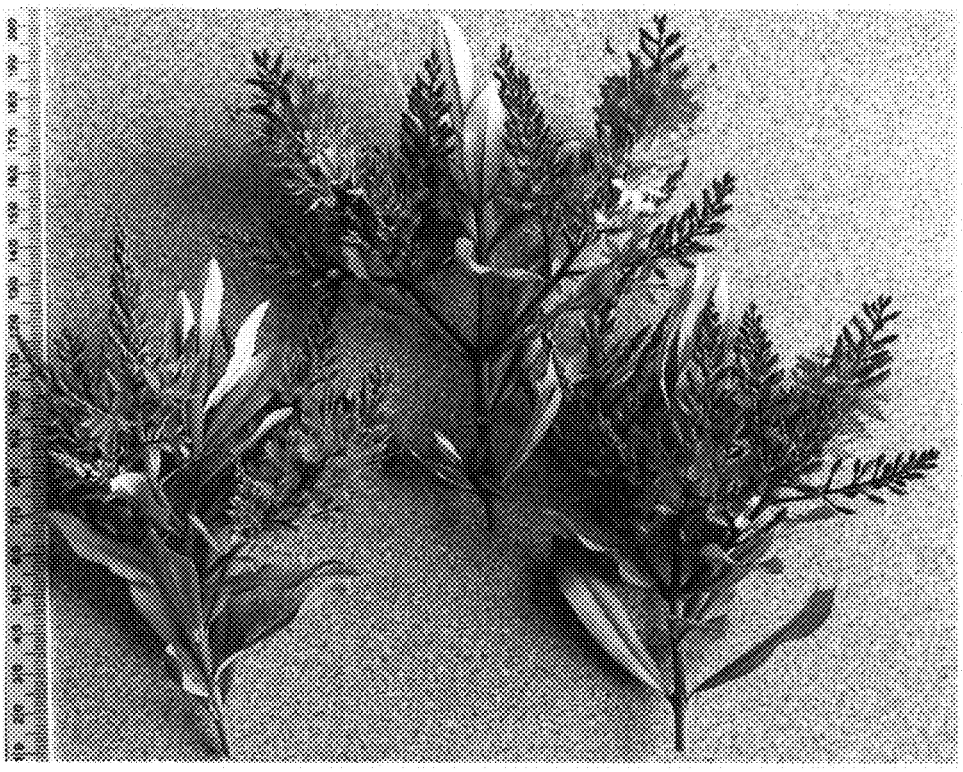

The photograph in FIG. 2 provides a close-up view of inflorescences of 'Celebration'.

Figure 3:
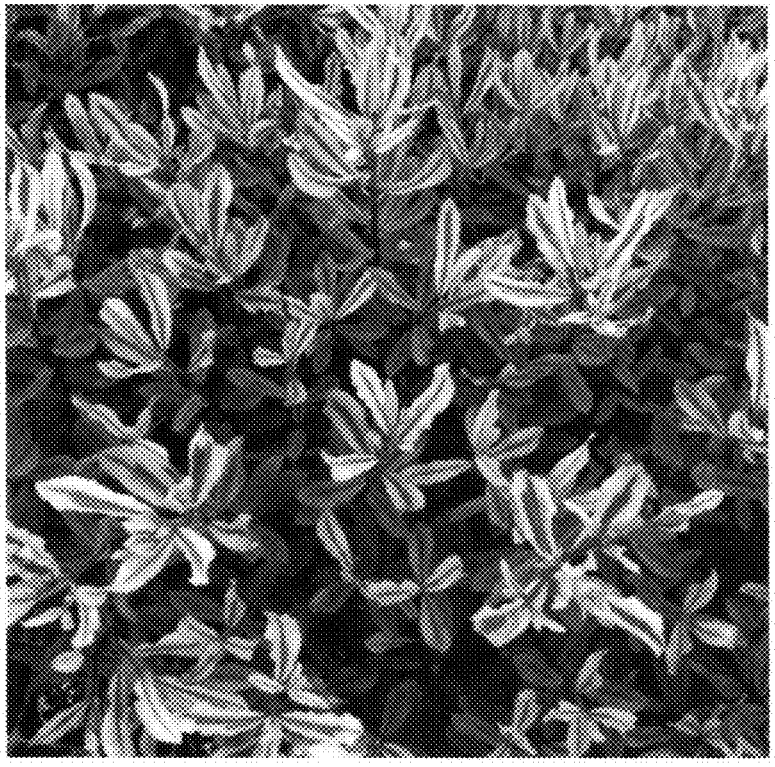

The photograph in FIG. 3 provides a close-up view of the foliage of 'Celebration'.

The colors in the photographs are as close as possible with the photographic and printing technology utilized and the color values cited in the detailed botanical description accurately describe the colors of the new *Hebe*.

DETAILED BOTANICAL DESCRIPTION OF THE PLANT

The following is a detailed description of six month-old plants of the new cultivar as grown in three-liter containers in an un-heated greenhouse Hampshire, The United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming period*.—An average of five weeks starting from mid-May in Spalding, The United Kingdom.

*Plant type*.—Evergreen shrub.

*Plant habit*.—Compact and rounded.

*Height and spread*.—An average of 25 cm in height and 30 cm in width as a six month old plant.

*Cold hardiness*.—At least tolerant to U.S.D.A. Zone 8.

*Diseases and pests*.—Not more resistant or susceptible to pests and diseases compared to other *Hebe* varieties.

*Root description*.—Fibrous to slightly fleshy and 164D in color.

*Growth rate*.—Moderate.

*Propagation type*.—Softwood stem cuttings.

*Root development*.—Roots initiate in about 28 days and a rooted plug will fully develop in up to a 5-liter container in about 6 months.

Branch description:

*Branch size*.—An average of 16 cm in length and 3 mm in diameter.

*Branch shape*.—Rounded.

*Branch color*.—Young branches; a blend between 144B to 144C and 183B to 183D, mature branches; 187A, older bark; 175A to 175B.

*Branch surface*.—Smooth, slightly glossy, and puberulent.

*Branch strength*.—Medium strength.

*Internode length*.—An average of 1 cm.

*Branching habit*.—Well-branched.

*Branch angle*.—An average of 45°.

Foliage description:

*Leaf shape*.—Narrowly elliptic to obelleptic.

*Leaf division*.—Single.

*Leaf base*.—Cuneate.

*Leaf apex*.—Acute.

*Leaf venation*.—Pinnate, young leaf upper surface; 59A, young leaf lower surface and mature leaf upper and lower surfaces; inconspicuous, color matches the leaf surface.

*Leaf margins*.—Entire.

*Leaf attachment*.—Petiolate.

*Leaf arrangement*.—Opposite and decussate.

*Leaf surface*.—Glabrous and slightly glossy on upper surface and glabrous and dull on lower surface.

*Leaf color*.—Variegated, young leaves; upper young surface a blend between 1D and 144A with irregular central stripe 138A to 138B and lower surface a blend between 1C and 144C with irregular central stripe 191A to 191B, mature leaves; upper surface 137B with irregular central stripe N137D and lower surface 147C, all leaves, except the very oldest, have a very thin margin 59A in color.

*Leaf number*.—An average of 20 per lateral branch.

*Leaf size*.—An average of 3.9 cm in length and 1 cm in width.

*Leaf aspect*.—Held upright to horizontal to stem.

*Leaf fragrance*.—None.

*Petiole*.—An average of 2 mm in length, glabrous surface, 187B in color, medium strength.

Flower description:

*Inflorescence type*.—Raceme.

*Inflorescence size*.—An average of 1.1 to 2 cm in length and width.

*Inflorescence lastingness*.—Self cleaning, an inflorescence will last an average of 5 weeks, an individual floret will last an average of 10 days (self-cleaning).

*Flower shape*.—Campanulate.

*Flower fragrance*.—None.

*Flower quantity*.—An average of 45 florets per inflorescence.

*Flower arrangement*.—Axillary racemes.

*Flower aspect*.—Upwards and outwards.

*Flower size*.—An average of 4 to 5 mm in depth and diameter.

*Peduncles*.—Medium strength, an average of 2 cm in length and 1.25 mm in diameter, N186C to N186D in color, held at an average angle of 45° to lateral branch, puberulent surface.

*Pedicels*.—Strong strength, an average of 2.5 mm in length and 0.5 mm in diameter, held at an average angle of 45° to peduncle, 186C in color.

*Bracteole*.—An average of 3 mm in length and 1 mm in width, color; 144C with narrow stripe 138B, puberulent surface.

*Flower buds*.—Ellipsoid in shape, an average of 6 mm in length and 1 mm in diameter, 72B in color, glabrous surface.

*Calyx*.—Rotate in shape, an average of 2 mm in length and 1 cm in diameter, color; 143A heavy suffused with 186A, puberulent surface.

*Sepals*.—4, narrow ovate in shape, entire margins, rotate arrangement, acute tip, base cuneate with lower 50% fused, dull and smooth surface, color upper and lower surfaces 148C, an average of 3 mm in length and 1 mm in width.

*Corolla*.—An average of 11 mm in diameter and 5 mm in depth, smooth surface.

*Corolla lobes*.—4, ovate in shape, an average of 5 mm in length and 3 mm in width, fused base, entire margins, acute apex, dull and smooth upper and lower surfaces, color; upper and lower surface N78A fading through 72B, 70A, and 76B as the flower ages, paler in color towards the base.

*Corolla tube*.—3 mm in depth and 2 mm in width, dull and smooth on both surfaces, color matches lobe coloration.

Reproductive organs:

*Gynoecium*.—1 Pistil, an average of 1.1 cm in length, stigma; capitate in shape; an average of <0.5 mm in length and width, and N79C in color, style; linear in shape, an average of 8 mm in length and less than 0.5 mm in width, and N781A in color, ovary; superior, ovoid in shape, an average of 2 mm in length and 1 mm in width, and 148C in color.

*Androecium.*—2 stamens, anthers are dorsifixed, ovoid in shape, an average of 1.5 mm in length and 0.5 mm in width, 77A in color, filaments; an average of 9 mm in length and <0.5 mm in width, N178B to N178C in color, pollen is moderate in quantity and 163C in color.

*Seed.*—Very small in size less than 0.2 mm in length and diameter, smooth, dull surface, 200C in color.

It is claimed:

1. A new and distinct cultivar of *Hebe* plant named 'Celebration' as herein illustrated and described.

* * * * *